(12) United States Patent
Torrence et al.

(10) Patent No.: US 8,952,196 B2
(45) Date of Patent: Feb. 10, 2015

(54) REMOVAL OF AROMATICS FROM CARBONYLATION PROCESS

(75) Inventors: G. Paull Torrence, League City, TX (US); Ronald David Shaver, Houston, TX (US); Yaw-Hwa Liu, Missouri City, TX (US)

(73) Assignee: Celanese International Corporation, Dallas, TX (US)

( * ) Notice: Subject to any disclaimer, the term of this patent is extended or adjusted under 35 U.S.C. 154(b) by 358 days.

(21) Appl. No.: 13/462,979

(22) Filed: May 3, 2012

(65) Prior Publication Data

US 2012/0283472 A1    Nov. 8, 2012

Related U.S. Application Data

(63) Continuation-in-part of application No. 13/101,781, filed on May 5, 2011, now Pat. No. 8,697,908.

(51) Int. Cl.
*C07C 51/12*    (2006.01)

(52) U.S. Cl.
CPC ..................................... *C07C 51/12* (2013.01)
USPC .......................................................... 562/519

(58) Field of Classification Search
CPC ..................................................... C07C 51/12
See application file for complete search history.

(56) References Cited

U.S. PATENT DOCUMENTS

| | | |
|---|---|---|
| 3,769,329 A | 10/1973 | Paulik et al. |
| 4,007,130 A | 2/1977 | Leach et al. |
| 4,628,041 A | 12/1986 | Smith et al. |
| 4,894,477 A | 1/1990 | Scates et al. |
| 4,908,477 A | 3/1990 | Hartmann et al. |
| 4,994,608 A | 2/1991 | Torrence et al. |
| 5,001,259 A | 3/1991 | Smith et al. |
| 5,026,908 A | 6/1991 | Smith et al. |
| 5,144,068 A | 9/1992 | Smith et al. |
| 5,300,715 A | 4/1994 | Vora |
| 5,466,876 A | 11/1995 | McClarron et al. |
| 5,696,284 A | 12/1997 | Baker et al. |
| 5,731,252 A | 3/1998 | Warner et al. |
| 5,877,347 A | 3/1999 | Ditzel et al. |
| 5,877,348 A | 3/1999 | Ditzel et al. |
| 5,883,295 A | 3/1999 | Sunley et al. |
| 5,917,089 A | 6/1999 | Howard |
| 5,932,764 A | 8/1999 | Morris |
| 5,942,460 A | 8/1999 | Garland et al. |
| 6,106,702 A | 8/2000 | Sohn et al. |
| 6,143,390 A | 11/2000 | Takamiya et al. |
| 6,339,171 B1 | 1/2002 | Singh et al. |
| 6,346,645 B1 | 2/2002 | Kulprathipanja et al. |
| 6,627,770 B1 | 9/2003 | Cheung et al. |
| 6,657,078 B2 | 12/2003 | Scates et al. |
| 7,005,541 B2 | 2/2006 | Cheung et al. |
| 7,223,886 B2 | 5/2007 | Scates et al. |
| 2005/0197513 A1 | 9/2005 | Trueba et al. |
| 2006/0247466 A1 | 11/2006 | Zinobile et al. |
| 2006/0293537 A1 | 12/2006 | Trueba et al. |
| 2008/0287706 A1 | 11/2008 | Powell et al. |
| 2008/0293966 A1 | 11/2008 | Scates et al. |
| 2009/0107833 A1 | 4/2009 | Warner |
| 2009/0270651 A1 | 10/2009 | Zinobile et al. |

FOREIGN PATENT DOCUMENTS

| | | |
|---|---|---|
| DE | 102007030440 | 1/2009 |
| EP | 0849248 | 6/1998 |
| GB | 2334955 | 9/1999 |

OTHER PUBLICATIONS

Kim et al, Catalysis Today, Adsorption—Desorption Characteristics of VOCs over Impregnated Activated Carbons, 2006, 111 pp. 223-228.*
International Preliminary Report on Patentability for PCT/US2012/036283 mailed Nov. 14, 2013.
Collins et al., "Process for removal of traces of amines from refined methanol using ion-exchange resins," Chemistry and Industry, Feb. 19, 1972, pp. 173-174.
Jones, J. H., "The Cativa Process for the Manufacture of Acetic Acid", Platinum Metals Review, 44 (3), pp. 94-105 (2000).
International Search Report and Written Opinion for PCT/US2012/036278 mailed Sep. 5, 2012.
International Search Report and Written Opinion for PCT/US2012/036283 mailed Sep. 5, 2012.

* cited by examiner

*Primary Examiner* — Paul A Zucker

(57) ABSTRACT

The invention relates to processes for removing aromatics from the reactants that are fed to a carbonylation reactor. The aromatics are removed using a guard bed that comprises an adsorbent.

20 Claims, 2 Drawing Sheets

US 8,952,196 B2

REMOVAL OF AROMATICS FROM CARBONYLATION PROCESS

CROSS REFERENCE TO RELATED APPLICATION

The present invention is a continuation-in-part of U.S. application Ser. No. 13/101,781, filed on May 5, 2011, the entire contents and disclosure of which is incorporated by reference.

FIELD OF THE INVENTION

The present invention is directed to a method for removing aromatics from a reactant composition that is fed to a carbonylation process using a guard bed that comprises an adsorbent.

BACKGROUND OF THE INVENTION

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105 the entire content and disclosure of which is hereby incorporated by reference. The reaction solution is withdrawn from the reactor and purified to obtain acetic acid.

In the commercial production of acetic acid, there are several processes for removing catalysts, promoters and impurities formed during the carbonylation reaction when purifying the acetic acid. In addition to impurities formed during the carbonylation process, some reactants, depending on their source and purity, may contain trace impurities that may pass through the carbonylation process. These "pass-through" impurities may be difficult to remove using conventional purification techniques. Thus, the resulting acetic acid may contain impurities that form an off-specification product that is not suitable for the desired end use.

As a result, the need exists for additional processes for removing impurities, and in particular pass-through impurities, in the production of acetic acid.

SUMMARY OF THE INVENTION

In a first embodiment, the present invention is directed to a carbonylation process for producing a carbonylation product having a low aromatic content, the process comprising contacting a reactant composition that comprises (i) a reactant selected from the group consisting of methanol, methyl acetate, methyl formate, dimethyl ether, and mixtures thereof and (ii) an aromatic compound, preferably at least 1 wppm the aromatic compounds, based on total weight of the reactant composition, with a guard bed that comprises an adsorbent to form a de-aromatic reactant composition, reacting carbon monoxide with the de-aromatic reactant composition in a reactor containing a reaction medium to produce a reaction solution comprising acetic acid, and wherein the reaction medium comprises water, acetic acid, methyl acetate, methyl iodide, and a catalyst, and withdrawing a reaction solution from the reactor, wherein the reaction solution is substantially free of aromatic compounds. In one embodiment, the adsorbent comprises activated carbon, zeolites, activated amorphous clays, metal oxides, or silicaceous adsorbents. At least 6 milligrams of the adsorbent may be used for each gram of the reactant composition. In one embodiment, the aromatic compound is selected from the group consisting of benzene, toluene, xylenes, ethylbenzene, naphthalene, benzene derivatives, and mixtures thereof. In one embodiment, the de-aromatic reactant composition comprises less than 40 wppm the aromatic compounds, based on total weight of the de-aromatic reactant composition, and has a lower concentration of the aromatic compounds than the reactant composition. In one embodiment, at least 40% of the aromatic compounds are removed by the guard bed.

In a second embodiment, the present invention is directed to a carbonylation process for producing a carbonylation product having a low aromatic content, the process comprising measuring a concentration of aromatic compounds in a reactant composition, wherein the reactant is selected from the group consisting of methanol, methyl acetate, methyl formate, dimethyl ether, and mixtures thereof, contacting the reactant composition with a guard bed that comprises an adsorbent when the measured concentration of aromatic compounds is more than 1 wppm to form a de-aromatic reactant composition having less than 40 wppm, provided that the concentration of the aromatic compounds of the de-aromatic reactant composition is less than that the concentration of the aromatic compounds of the reactant composition, reacting carbon monoxide with the de-aromatic reactant composition in a reactor containing a reaction medium to produce a reaction solution comprising acetic acid, and wherein the reaction medium comprises water, acetic acid, methyl acetate, methyl iodide, and a catalyst, and withdrawing a reaction solution from the reactor, wherein the reaction solution is substantially free of aromatic compounds. In one embodiment, the aromatic compounds are measured using an on-line analyzer selected from the group consisting of gas chromatography, and UV spectrophotometry. In one embodiment, the process further comprises adding a fresh reactant to the reactant composition prior to the guard bed, wherein the fresh reactant comprises less aromatic compounds than the reactant composition.

In a third embodiment, the present invention is directed to a carbonylation process for contacting a reactant composition that comprises (i) a reactant selected from the group consisting of methanol, methyl acetate, methyl formate, dimethyl ether, and mixtures thereof, (ii) an aromatic compound, and (iii) an amine, with a guard bed that comprises an adsorbent to form a de-aromatic reactant composition, contacting the de-aromatic reactant composition with an exchange resin, preferably a sulfonated styrene-divinylbenzene copolymer, to produce a purified de-aromatic reactant composition having a reduced amine content, reacting carbon monoxide with the purified de-aromatic reactant composition in a reactor containing a reaction medium to produce a reaction solution comprising acetic acid, and wherein the reaction medium comprises water, acetic acid, methyl acetate, methyl iodide, and a catalyst, and withdrawing a reaction solution from the reactor, wherein the reaction solution is substantially free of aromatic compounds and amine compounds. In one embodiment, the purified de-aromatic reactant composition comprises less than 1 wppm amine, based on total weight of the purified de-aromatic reactant composition. The reactant composition may comprise less than 100 wppm of the amine, based on total weight of the reactant composition.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
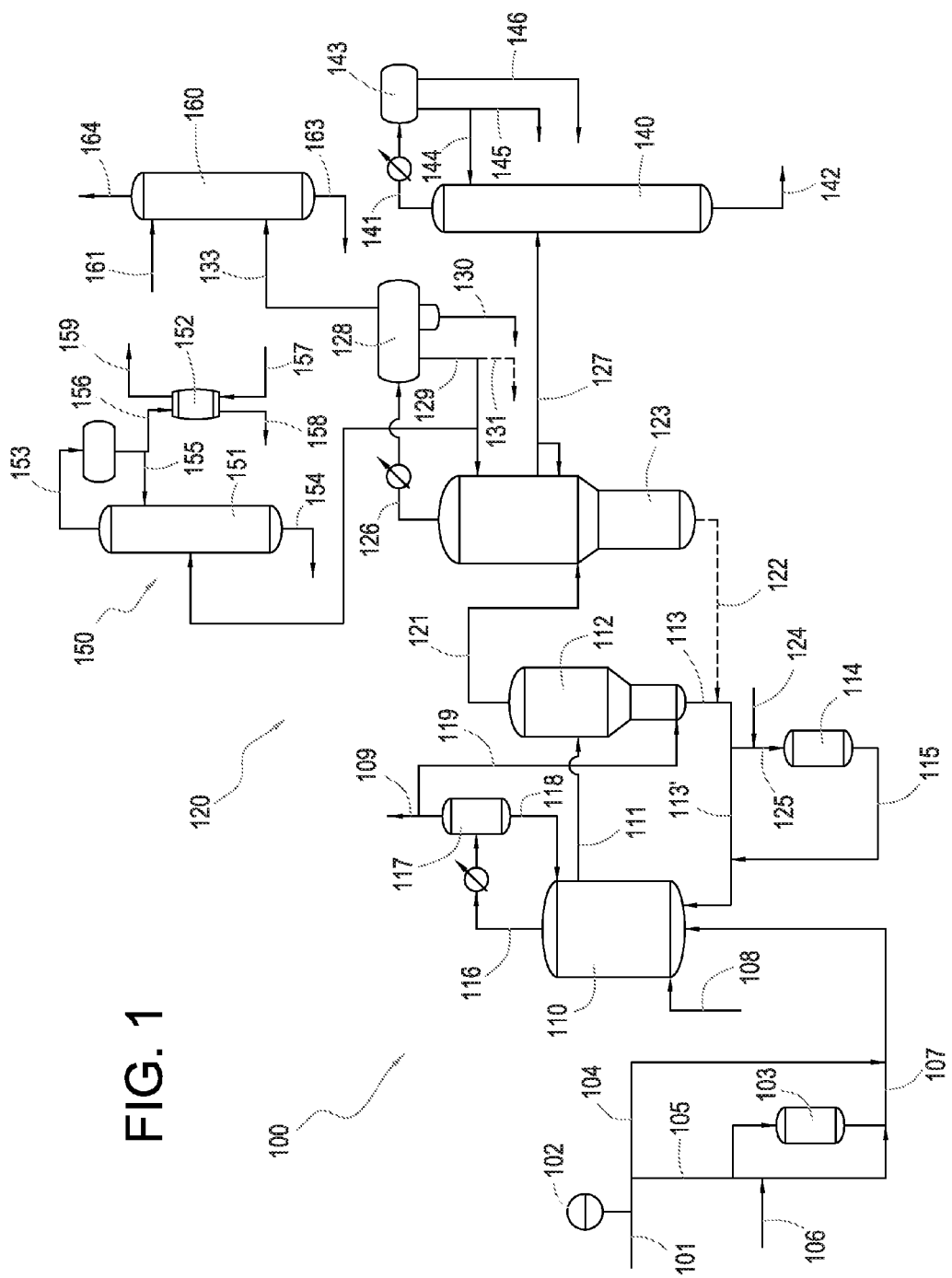
FIG. 1 illustrates a carbonylation process having a guard bed according to an embodiment of the present invention.

The present invention generally relates to acetic acid production by methanol carbonylation under low water conditions. The methanol reactant compositions fed to the carbonylation process may contain, depending on grade, low levels of impurities, including one or more aromatic and/or amine compounds. The aromatic compounds may be selected from the group consisting of benzene, toluene, xylenes, ethylbenzene, naphthalene, other benzene derivatives, and mixtures thereof. Typically, the aromatic compounds may be contaminants in the methanol reactant composition caused, for example, by transporting the methanol reactant in a trailer, container, pipe, or barge that previously contained a petrochemical or a compound other than the methanol reactant. The aromatic compounds may be present in amounts of at least 1 wppm, e.g., at least 50 wppm or at least 75 wppm. In terms of ranges, the aromatic compounds may be present in amounts from 1 to 800 wppm, e.g., from 50 to 500 wppm, or from 50 to 100 wppm.

Such aromatic compounds are difficult to separate from acetic acid and thus additional purification after the carbonylation process may not be effective in removing the aromatic compounds. As a result, the aromatic compounds may pass through the acetic acid separation train along with the acetic acid, resulting in off-spec acetic acid product. In one embodiment, a guard bed that comprises an adsorbent is used to remove a majority of the aromatic compounds from the reactant composition that is fed to the carbonylation reactor. The resulting de-aromatic reactant composition has a lower aromatic concentration than the reactant composition that is fed to the guard bed. For example, the guard bed may remove at least 40% of the aromatic compounds from the reactants, e.g., at least 60%, at least 75% or at least 90%.

The adsorbents for the guard beds are preferably suited for removing aromatic compounds in the liquid phase. Suitable adsorbents may include, for example, activated carbon, zeolites, activated amorphous clays, metal oxides (iron oxide, zirconium oxides, alumina, titania), or silicaceous adsorbents, (silicon oxide or silica gel). The adsorbent may have a surface area, as determined by nitrogen gas absorption, that is at least 100 m$^2$/g, e.g., at least 250 m$^2$/g or at least 500 m$^2$/g. More preferably, activated carbon is used as the adsorbent. Activated carbon may be produced from a variety of carbonaceous raw materials, such as coconut shells, nutshells, coal, and lignite. Granular activated carbon may be used in a guard bed that has a 20×40, 12×40, 8×20, 8×30 size. In one embodiment, at least 6 milligrams of absorbent may be used for each gram of the reactant composition that passes through the guard bed, and more preferable at least 10 milligrams or at least 100 milligrams. The de-aromatic reactant composition that exits the guard bed may have an aromatic concentration of less than 40 wppm, e.g., less than 30 wppm or less than 20 wppm. In terms of ranges, the aromatic concentration in the de-aromatic reactant composition may range from 0.1 wppm to 40 wppm, e.g., from 0.1 to 30 wppm or from 0.1 to 20 wppm. In some embodiments, the guard bed may be capable of removing substantially all of the aromatic compounds from the reactant composition. Removing the aromatic compounds from the reactant composition reduces the aromatic concentration of the reaction solution from the carbonylation reactor so that the reaction solution also comprises less than 40 wppm aromatic compounds.

One problem with aromatic compounds in the reactant composition is that they may not be detected until the acetic acid is being used, e.g., as a starting material for synthesis of another chemical, such as vinyl acetate. In one embodiment, prior to the reactant composition entering the carbonylation reactor, a portion of the reactant composition passed through an on-line gas chromatograph or UV spectrophotometer to monitor aromatic concentration.

In FIG. 1, a reactant composition, preferably methanol, in line 101 is fed to the carbonylation process 100. A gas chromatograph 102 detects the aromatic concentration of the reactant composition in line 101. When the aromatic concentration is low, e.g., less than 0.1 wppm, the reactant composition, or a portion thereof, may be directed directly to carbonylation reactor 110 via line 104. When the aromatic concentration is greater than 0.1 wppm, and more preferably greater than 50 wppm, the reactant composition is directed to line 105. In one embodiment, reactant composition, or a portion thereof, in line 105 may pass through guard bed 103 to remove the aromatic compounds using an adsorbent. Guard bed 103 is a fixed bed in FIG. 1. In other embodiments, guard beds may comprise a fluidized bed, or moving bed. Single or multiple beds may be used, in series and/or in parallel. Guard bed 103 may be any practical size and preferably is sized so that the pressure drop across the bed is less than 100 kPa, e.g., less than 75 kPa or less than 50 kPa. Guard bed 103 optionally may operate at a temperature from 0° C. to 40° C., e.g., from 15° C. to 30° C. In one embodiment, guard bed 103 is adjacent to an inlet for reactor 110. The adsorption of aromatic compounds is exothermic and the adsorbent should be sufficiently durable so as to withstand the exothermic temperature increase.

In another embodiment, the reactant composition, or a portion thereof, in line 105 may be diluted with another reactant composition via stream 106 that is substantially free of aromatic compounds. Without being bound by theory, when the concentration of aromatic compounds in the reactant composition is more than 50 wppm, guard bed 103 may be inefficient in removing the aromatic compounds and thus it may be more effective to dilute the reactant composition so long as a source of the reactant composition that is substantially free of aromatics is available. In some exemplary embodiments, stream 106 may comprise more than 50 wppm aromatic compounds, more than 75 wppm aromatic compounds or more than 100 wppm aromatic compounds. In some embodiments, not shown, the reactant composition may be diluted and then passed to guard bed 103.

The resulting de-aromatic reactant composition in line 107 that exits guard bed 103 and/or is diluted with stream 106 may be fed directly to carbonylation reactor 110 as shown in FIG. 1.

The rate of flow of reactant composition 101 through guard bed 103 during removal of aromatic compounds and corrosive metals, in general, may vary from 0.8 to 80 bed volumes per hour (BV/hr), e.g., from 1 to 35 BV/hr or more preferably from 1 to 25 BV/hr. In an exemplary embodiment, 2.5 to 3 BV/hr may provide sufficient contact time for the adsorption of aromatic compounds.

In one embodiment, guard bed 103 may be regenerated by switching the feed to the bed and passing a solution that desorbs the aromatic compounds. The aromatic compounds are completely removed from the bed prior to switching the reactant composition feed. Regenerating may include thermal, solvent, and/or chemical regeneration, including wet air oxidation (WAO). Thermal regeneration, at temperature from 500° C. to 900° C., and WAO regenerate of the bed may be accompanied by simultaneous destruction of the adsorbed compounds from the porous structure. Chemical or solvent regeneration may use a regenerant, such as methanol, ethanol, acetone, or formic acid, along with water rinsing.

In addition to aromatic compounds, the methanol reactant composition may also contain one or more amine compounds. Unlike aromatic compounds, amines in the methanol reactant composition may be derived from the methanol synthesis process. The amine compounds may build up in the carbonylation process and, in particular, in the carbonylation reactor and accompanying flasher. Amine compounds tend to form inorganic amine salts, which tend to build up in the reactor and/or flasher. As a result, corrosion tends to increase in the reactor and associated flasher, resulting in additional formation of corrosion metals. The presence of additional corrosion metals requires further processing to maintain a low concentration of corrosion metals in the reactor and/or flasher. Thus, the presence of amine compounds presents operability issues that may be difficult to control and may lead to inefficient production.

One difficulty in removing amine compounds from a carbonylation process stream is that other impurities, in particular corrosion metal contaminants, tend to dominate impurity removal dynamics. Typically, corrosion metal contaminants are removed from process streams using exchange resins. In some exemplary cases, acid solvents such as acetic acid may be added to the exchange resin to improve removal efficiency of corrosion metal contaminants. The acidic environment may favor removal of corrosion metal contaminants. However, favoring the removal of corrosion metals contaminants tends to reduce the ability of the exchange resins to remove other impurities such as amine compounds. Previous efforts have focused on removing corrosion metal contaminants using exchange resins, but have failed to recognize the need to remove other impurities such as the aforementioned aromatic and/or amine compounds.

In one embodiment, the processes of the present invention overcome the problems associated with the presence of aromatic and/or amine compounds and the removal of the amine compounds from carbonylation process streams.

In particular for amines, the present invention addresses problems relating to removal of amine compounds from one or more carbonylation process streams that also contain corrosion metal contaminants. Generally, process streams that contain corrosion metal contaminants and amine compounds are acidic. The typical acidic conditions in an exchange resin favor binding of the corrosion metal contaminants over amine compounds. Thus, the exchange resins would be ineffective in removing amine compounds in an acidic environment. In some embodiments the acidity within the exchange resin is reduced by mixing the process stream, containing corrosion metal contaminants and amine compounds, with a slipstream to form an aqueous stream having a water concentration of greater than 50 wt. %, e.g., greater than 60 wt. %, greater than 75 wt. % or greater than 85 wt. %. In terms of ranges, the aqueous stream may have a water concentration from 50 wt. % to 90 wt. %, e.g., from 50 wt. % to 85 wt. % or from 60 wt. % to 85 wt. %. The aqueous stream may create a weakly acidic environment, optionally having a pH above about 4.5, or a non-acidic environment in the exchange resin. The water concentration of the aqueous stream may be controlled by mixing a slipstream with the process stream, or by directly feeding the slipstream to the exchange resin, to dilute the process stream containing corrosion metal contaminants and amine compounds. Multiple slipstreams may be mixed with the process stream, provided that the aqueous stream has a high water concentration. Using the aqueous stream, the removal of amine compounds may be improved, even in the presence of corrosion metal contaminants.

The slipstream may comprise methanol, water, methyl acetate, methyl iodide or a mixture thereof. In one embodiment, the slipstream may comprise methanol, water, or mixtures thereof. Preferably, the slipstream comprises water and a minor amount of organics. Also, the slipstream may comprise acetic acid, e.g., amounts less than 20 wt. %, optionally less than 10 wt. % or less than 5 wt. %. In one embodiment, the slipstream may be a dilute acetic acid stream. The slipstream may be obtained from one or more of the process stream within the system. In addition, the slipstream, in some embodiments, may be obtained from a portion of the reactant feed stream. The slipstream may be added to the process stream before contacting the exchange resin or may be added directly to the exchange resin.

In some embodiments of the present invention, the term "process stream" refers to any stream separated during purification that is retained in the carbonylation process. In one embodiment, aromatic compounds are removed from the reactant composition fed to the carbonylation reactor and not the carbonylation process stream. Generally, waste streams that are purged or the resultant acetic acid product stream are not referred to as process streams. The process stream(s) may be recycled, directly or indirectly, to the carbonylation reactor. In one embodiment, one or more process stream may be treated with an exchange resin to remove corrosion metal contaminants and amine compounds. Also, some process stream(s) may be used as slipstream(s) to form the aqueous stream that contacts the exchange resin. In these cases, the process stream used to form the aqueous stream is different from the process stream treated via the exchange resin.

Corrosion metal contaminants, in particular, iron, nickel, chromium and molybdenum may be present in any of the process streams of the carbonylation process. In general, these corrosion metal contaminants have an adverse effect on the acetic acid production rate and the overall stability of the process. Therefore, an ion exchange resin is placed within the carbonylation process to remove these corrosion metal contaminants, as well as amine compounds, from the process streams.

Returning to FIG. 1, de-aromatic reactant composition in line 107 and carbon monoxide in line 108 are fed to carbonylation reactor 110. A reaction solution in line 111 is withdrawn and fed to flasher 112. A catalyst solution process stream 113 is withdrawn from the base of flasher 112, and a portion thereof is passed through exchange resin bed 114 containing the exchange resin via line 125. The exiting stream is recycled via line 115 to reactor 110. It should be understood, that any of the process streams can be treated via the ion exchange resin to remove amine compounds and/or metal contaminants therefrom. Process stream 113 should be at a temperature, such as less than 120° C., that does not deactivate the resin. If necessary process stream 113 may be cooled.

The present invention may be applied in any suitable methanol carbonylation process. Exemplary carbonylation processes that may be used with embodiments of the present invention include those described in U.S. Pat. Nos. 7,223,886, 7,005,541, 6,657,078, 6,339,171, 5,731,252, 5,144,068, 5,026,908, 5,001,259, and 4,994,608, and U.S. Pub. Nos. 2008/0287706, 2008/0293966, 2009/0107833, and 2009/0270651, the disclosures of which are hereby incorporated by reference. The exemplary carbonylation system depicted herein may also include further systems and components that may be used with embodiments of the present invention include those described in these patents. It should be understood that the carbonylation system shown in the figures is exemplary and other components may be used with the scope of the present invention. The methanol carbonylation process may comprise a carbonylation section and a purification section. The embodiments of the present invention are not limited by the configuration of the carbonylation or purification sections. Thus, any suitable purification section may be used in combination with any of the embodiments of the present invention.

In an exemplary carbonylation process as shown in FIG. 1, carbon monoxide is fed via stream 108 to a lower portion of reactor 110. Other reactants are similarly fed via stream 107. Preferably, these reactants are substantially free of aromatic and/or amines compounds, which have been removed by at least one of guard bed 103 and/or exchange resin 114. Reactant composition in stream 107 supplies to reactor 110 at least one reactant comprising methanol, methyl acetate, methyl formate, dimethyl ether, and/or mixtures thereof. In preferred embodiments, reactant composition in stream 107 supplies methanol and methyl acetate. Optionally, reactant composition in line 101 may be connected to one or more vessels (not shown) that store fresh reactants for the carbonylation process. Due to containments in those vessels, the aromatic compounds may be present in reactant composition 101 when transferred to process 100. In addition, there may be a methyl iodide storage vessel (not shown) and/or catalyst vessel (not shown) connected to reactor 110 for supplying fresh methyl iodide and catalyst as needed to maintain reaction conditions. In other embodiments, all or some of the methanol and/or methanol derivatives supplied to reactor 110 may be in the form of scrubbed methanol from another location in the system or as a product or by-product of another system.

One or more process streams from carbonylation process 100 may be recycled to reactor 110. In some embodiments, recycle feed streams comprising the reaction medium components, e.g., residual/entrained catalyst, or acetic acid, are directed to the reactor. Preferably, there are multiple process streams that are recycled and fed, in combination or separately, to reactor 110. For example, one or more process streams from purification section 120 may be fed to reactor 110. Preferably, the recycled process streams are introduced in the lower portion of reactor 110.

In certain embodiments of the invention, reactant composition in line 107 comprises methanol and/or methanol derivatives. Suitable methanol derivatives include methyl acetate, dimethyl ether, methyl formate, and mixtures thereof. In one embodiment, a mixture of methanol and methanol derivatives is used as a reactant in the process of the present invention. Preferably, methanol and/or methyl acetate are used as reactants. At least some of the methanol and/or methanol derivatives will be converted to, and hence be present as, methyl acetate in the reaction medium by reaction with acetic acid product or solvent. The concentration of methyl acetate in the reaction medium is preferably in the range from 0.5 wt. % to 70 wt. %, e.g., from 0.5 wt. % to 50 wt. %, or from 1 wt. % to 35 wt. %, of the total weight of the reaction medium.

In embodiments of the present invention, methanol fed to the carbonylation reaction, after the aromatic compounds are reduced and/or removed, may also contain one or more amine compounds. Conventional acetic acid production processes used higher grades of methanol, which limits the reactant supply sources and increases costs of production. Lower grades of methanol may contain higher amounts of amine compounds. Even higher grades of methanol may contain amine compounds. For example, even 1 wppm of trimethylamine may be sufficient to give methanol a distinct odor. Also, some amine compounds may be present in the reaction medium. The amine compounds include alkyl amines, aryl amines, heterocyclic amines, and mixtures thereof. Alkyl and aryl amines may include trimethylamine, triethylamine, dimethylethyl amine, diethylmethyl amine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, and benzyldimethylamine. Heterocyclic amines include piperidines, piperazines, pyridines, pyridazines, pyrazines, pyrimidines, triazines, pyrrolidines, pyrroles, pyrazoles, pyrazolines, pyrazolidines, imidazolines, imidazolidines, imidazoles, and triazoles, and substituted heterocyclic compounds thereof. The amine compounds may also comprise diamines, triamines, and tetramines, such as tetramethylhexamethylendiamine, tetramethylethylendiamine, tetramethylpropylendiamine, tetramethylbutylendiamine, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, and diisobutylentriamine. The amine present in the methanol feed streams may vary depending on the grade of the methanol and the type of impurity. In one embodiment, the methanol feed comprises less than 100 wppm amine, based on nitrogen content, e.g., less than 20 wppm or less than 1 wppm. In terms of ranges, the methanol feed stream comprises from 0.1 to 100 wppm amine compounds, based on nitrogen content, e.g., from 0.5 to 50 wppm or from 1 to 20 wppm.

Carbon monoxide feed stream 108 may be essentially pure or may contain small amounts of inerts and impurities such as carbon dioxide, methane, nitrogen, hydrogen, noble gases, water and $C_1$ to $C_4$ paraffinic hydrocarbons. The presence of hydrogen in the carbon monoxide generated in situ by the water gas shift reaction is preferably kept low (e.g., less than 1 bar partial pressure or less than 0.5 bar partial pressure), as its presence may result in the formation of hydrogenation products. The partial pressure of carbon monoxide in the reaction is preferably in the range from 1 bar to 70 bar, e.g., from 1 bar to 35 bar, or from 1 bar to 15 bar.

In some embodiments of the invention, within reactor 110, methanol is reacted with carbon monoxide in a homogeneous catalytic reaction system comprising a reaction solvent, methanol and/or methanol derivatives, a Group VIII catalyst, at least a finite concentration of water and optionally an iodide salt.

Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]^-$ anion, as is well known in the art. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259, 5,026,908 and 5,144,068, the entireties of which are hereby incorporated by reference.

When an iridium catalyst is used, the iridium catalyst may comprise any iridium-containing compound that is soluble in the reaction medium. The iridium catalyst may be added to the reaction medium for the carbonylation reaction in any suitable form that dissolves in the reaction medium or is convertible to a soluble form. Examples of suitable iridium-containing compounds that may be added to the reaction medium include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$ and hexachloroiridic acid $[H_2IrCl_6]$. Chloride-free complexes of iridium such as acetates, oxalates and acetoacetates are usually employed as starting materials. The iridium catalyst concentration in the reaction medium is generally in the range of 100 to 6000 wppm. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

Other promoters and co-promoters may be used as part of the catalytic system of the present invention, as described in EP0849248, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the reaction medium and/or any liquid process streams recycled to the reactor from the purification and acetic acid recovery stage. When used, the promoter is suitably present in the reaction medium at a molar ratio of promoter to metal catalyst of 0.5:1 to 15:1, preferably 2:1 to 10:1, more preferably 2:1 to 7.5:1. A suitable promoter concentration is 400 to 5000 wppm.

A halogen co-catalyst/promoter is generally used in combination with the Group VIII metal catalyst component. Methyl iodide is a preferred as the halogen promoter. Preferably, the concentration of halogen promoter in the reaction medium is in the range 1 wt. % to 50 wt. %, and preferably 2 wt. % to 30 wt. %.

The halogen promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Water may be formed in situ in the reaction medium, for example, by the esterification reaction between methanol reactant and acetic acid product. In some embodiments, water is introduced to reactor 110 together with or separately from other components of the reaction medium. Water may be separated from the other components of reaction composition withdrawn from reactor 110 and may be recycled in controlled amounts to maintain the required concentration of water in the reaction medium. Preferably, the concentration of water maintained in the reaction medium is in the range from 0.1 wt. % to 16 wt. %, e.g., from 1 wt. % to 14 wt. %, or from 1 wt. % to 3 wt. % of the total weight of the reaction composition.

In accordance with a preferred carbonylation process of the present invention, the desired reaction rates are obtained even at low water concentrations by maintaining, in the reaction medium, an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In reactor 110 the reaction medium is maintained, preferably automatically, at a predetermined level. This predetermined level may remain substantially constant during normal operation. Into reactor 110, methanol, carbon monoxide, and sufficient water may be continuously introduced as needed to maintain at least a finite concentration of water in the reaction medium. In some embodiments, carbon monoxide is continuously introduced into reactor 110. Carbon monoxide feed 108 is introduced at a rate sufficient to maintain the desired total reactor pressure. The temperature of reactor 110 may be controlled using heat exchangers in a pump around loop.

Acetic acid is typically manufactured in a liquid phase reaction at a temperature from 160° C. to 220° C. and a total pressure from 20 bar to 50 bar. In some embodiments of the invention, reactor 110 is operated at a temperature from 150° C. to 250° C., e.g., from 155° C. to 235° C., or from 160° C. to 220° C. The pressure of the carbonylation reaction is preferably from 10 to 200 bar, more preferably 10 to 100 bar and most preferably 15 to 50 bar.

A gaseous purge stream 116 may be vented from reactor 110 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Gaseous purge stream 116 may be scrubbed with acetic acid and/or methanol in recovery unit 117 to recover low boiling point components. The gaseous purge stream 116 may be partially condensed and the non-condensable portion from recovery unit 117 may return low boiling point components to the top of reactor 110 via stream 118. The non-condensable portion may comprise methyl acetate, water, and/or methyl iodide. Carbon monoxide in the gaseous purge stream may be vented in line 109 or fed via line 119 to base of flasher 112 to enhance rhodium stability.

Carbonylation product is drawn off from carbonylation reactor 110 at a rate sufficient to maintain a constant level therein and is provided to flasher 112 via stream 111. In flasher 112, the carbonylation product is separated in a flash separation step with or without the addition of heat to obtain a crude product stream 121 comprising acetic acid, and a liquid process stream 113, comprising a catalyst-containing solution. Aromatic compounds, if not removed, are concentrated in crude product stream 121. Generally, amine compounds are concentrated in liquid process stream 113 in the bottom of flasher 112 and substantially no amine compounds are carried over in crude product stream 121.

The catalyst-containing solution predominantly contains acetic acid, a metal compound of a carbonylation catalyst, e.g., a metal complex of rhodium and/or iridium, and the iodide salt, along with lesser quantities of methyl acetate, methyl iodide, and water. In addition, the catalyst-containing solution may contain minor amounts of corrosion metal contaminants, such as compounds containing iron, nickel, chromium, molybdenum, and the like. In one embodiment, liquid process stream 113 comprises corrosion metal contaminants in an amount from 0.025 wt. % to 1.0 wt. %, based on metal content, e.g., from 0.025 wt. % to 0.5 wt. % or from 0.025 to 0.1 wt. %. The catalyst-containing solution may also contain minor amounts of amine compounds. In one embodiment, liquid process stream 113 comprises amine compounds in an amount from 0.001 wt. % to 1.0 wt. % based on nitrogen content, e.g., from 0.01 to 0.5 wt. % or from 0.05 wt. % to 0.3 wt. %. In liquid process stream 113, the molar ratio of nitrogen in the amine to metal in the corrosion metal contaminants may be greater than 3:1, e.g., greater than 5:1 or greater than 10:1.

Liquid process stream 113 may be initially combined with optional stream 122 obtained from the bottoms of light ends column 123 in purification section 120, prior to being fed to exchange resin bed 114 via line 125. The bottoms of light ends column 123 in stream 120 may comprise acetic acid, a metal compound of a carbonylation catalyst, and impurities, such as the corrosion metal contaminants. A portion of liquid process stream 113 may be returned to reactor 110 via line 113', thus bypassing exchange resin bed 114. Depending on the reaction conditions, the amount of liquid process stream 113 directed to exchange resin bed 114 may be from 0.1 to 10% of the total mass flow of liquid process stream 113, and more preferably about 1%. Depending on the size of the resin bed 114, increase flows from liquid process stream 113 may pass through resin bed 114. The portion of liquid process stream 113 directed to exchange resin bed 114 is mixed with slipstream 124 to form aqueous stream 125. Aqueous stream 125 has a water concentration of greater than 50 wt. %, e.g., greater than 60 wt. %, greater than 75 wt. % or greater than 85 wt. %, and creates a weakly acidic or non-acidic environment in exchange resin bed 114. In terms of ranges aqueous stream 125 may have a water concentration from 50 wt. % to 90 wt. %, e.g., from greater than 50 wt. % to 85 wt. % or from 60 wt. % to 85 wt. %. Slipstream 124 may be mixed continuously or as needed to dilute liquid process stream 113. In other embodiments, slipstream 124 may be added directly to exchange resin bed 114.

The resins useful for removing amine compounds, as well as corrosion metal contaminants, from the process streams according to the present invention may include cation exchange resins either of the strong-acid or the weak-acid type. Both strong- and weak-acid type resins are readily available as commercial products. The weak-acid cation exchange resins are mostly copolymers of acrylic or methacrylic acids or esters or the corresponding nitriles, but a few of those marketed are phenolic resins. Preferably, strong-acid cation exchange resins are utilized. Strong-acid cation exchange resins predominantly comprise sulfonated styrene-divinylbenzene copolymers although some of the available resins of this type are phenol-formaldehyde condensation polymers. Amberlyst™ 15 (Dow) and Purolite™ CT275 (The Purolite Company) are exemplary commercial resins. Suitable resins may have a cation that corresponds to the cation employed in the halogen promoter. For purposes of illustrating the present invention, a cation exchange resin in its lithium form may be employed, such as those described in U.S. Pat. No. 5,731,252, the disclosure of which is hereby incorporated by reference.

Gel-type resins or macroreticular-type resins are suitable but the latter is preferred since organic components are present in the catalyst solutions being treated. Macroreticular resins are commonly employed in the catalytic art and require minimal water to maintain their swelling properties.

Contacting the catalyst-containing solution having corrosion metal contaminants and amine compounds with the resin may be performed in a stirred vessel wherein the resin is slurried with the catalyst solution with good agitation and the catalyst solution is then recovered by decantation, filtration, centrifuging, etc. However, treatment of the catalyst solutions is usually achieved by passing the catalyst-containing solution through a fixed-bed column of the resin. The catalyst regeneration can be carried out as a batch, semi-continuous or continuous operation either with manual or automatic control employing methods and techniques well known in the art of ion-exchange.

The ion exchange treatment may be performed at temperatures ranging from 0° C. to 120° C., e.g. from 20° C. to 90° C. Lower or higher temperatures are limited only by the stability of the resin to be employed. Chromium removal may be more efficient at the higher temperatures. At the higher temperatures, a nitrogen or CO purge is desirable. If temperatures above the boiling point of the catalyst solutions are employed, then operation under pressure may be required to maintain the solution in the liquid phase. However, pressure is not a critical variable. Generally, atmospheric pressure or a pressure slightly above atmospheric is employed but superatmospheric or subatmospheric pressures can be used if desired.

The rate of flow of liquid process stream 113 through exchange resin bed 114 during removal of amine compounds and corrosive metals, in general, may vary from 1 to 50 BV/hr, e.g. from 1 to 35 BV/hr or more preferably from 1 to 25 BV/hr. Depending on the resin and flow rate, higher bed volumes may be possible. For purposes of the present invention, higher bed volumes, e.g., greater than 20 BV/hr, and short residence time in exchange resin bed 114 may also advantageously favor removal of amine compounds.

Slipstream 124 may comprise methanol, water, methyl acetate, methyl iodide, acetic acid, or mixtures thereof. Slipstream 124 may be obtained from outside of the carbonylation system. Preferably slipstream 124 is supplied by one or more of the other process streams from purification section 120 or reactant composition in line 107. There are several available process streams to source slipstream 124. Examples of slipstream sources include, but are not limited to, light phase 131, heavy phase 130, residue 154 from PRS 150, raffinate 158 from PRS 150, low-boiling point process stream 163 from vent scrubber 160, light phase 145, heavy phase 146, and combinations thereof. Preferable slipstreams may comprise dilute acetic acid such as light phase 131 and light phase 145, which may be combined in part or whole with other streams.

In some embodiments, a portion of reactant composition in line 107, after aromatics are removed, may be used as slipstream 124. When reactant feed line 107 contains methanol, there may be amine compounds as discussed above. Mixing a portion of reactant feed line 107 with liquid process stream 113 may also reduce the amine compounds in reactant feed line 107 prior to being fed to reactor 110. Optionally, the entire reactant feed line 107 may be fed as a slipstream 124 to form aqueous stream 125.

Resin bed 114 produces an outflow stream 115 comprising a purified process stream comprising a reduced amine content. Outflow stream 115 is preferably returned to reactor 110. In one embodiment, outflow stream 115 contains less corrosion metal contaminants and amine compounds than aqueous stream 125 fed to resin bed 114. Higher water concentrations of the aqueous stream 125 tend to favor increased removal of corrosion metal contaminants and amine compounds. Preferably, outflow stream 115 has a reduced total corrosion metal and amine content. The reduced corrosion metal content may be less than 1 wppm based on total weight of outflow stream 115. Preferably outflow stream 115 is substantially free of corrosion metal contaminants. The reduced amine content may be less than 1 wppm based on total weight of outflow stream 115. In preferred embodiments, outflow stream 115 is substantially free of amine compounds.

After contacting the bed with liquid process stream 113, washing or rinsing of resin bed 114 with water or the carbonylation product from the process from which the catalyst being treated is derived, such as acetic acid, may be desired to remove the rhodium from the resin bed. The rinsing or washing is effected at similar flow rates as in the removal step.

After the resin has become exhausted, i.e., when the metal contaminants break through into the effluent, the resin can be regenerated by passing a solution of organic salts, preferably lithium salts, therethrough. Optionally, a lithium salt is used in the regenerating cycle at a concentration in the range from about 1 wt. % to about 20 wt. %. Quantities employed and regeneration procedures are well established in the art and commonly recommended by the resin manufacturers. Aqueous lithium acetate is preferred as a regenerating agent since the acetate anion is employed in the reaction system and is readily available for use. A further advantage is that its use eliminates the rinsing step normally required after the regeneration process when other regenerates are employed. To maximize corrosion metal regeneration capacity and to maximize resin bed column performance at relatively high concentrations of lithium acetate, the lithium acetate regeneration solution should contain some acetic acid, or product being produced, to avoid the formation of any insoluble corrosion metal compounds during the regeneration cycle. Precipitation of these compounds during the regeneration cycle may reduce the regeneration performance of the column and also cause plugging of the resin bed. Typically, acetic acid concentrations from about 0.1 to about 95 wt. % may be used, with acetic acid concentrations from about 0.1 to 20 wt. % being preferred.

The ion-exchange operation can be cyclic, where more than one resin bed is available for use. As the resin becomes exhausted in one resin bed, the slip stream of catalyst solution can be diverted to a fresh bed while the exhausted bed is subjected to regeneration.

Crude product stream 121 comprises acetic acid, methyl iodide, methyl acetate, water, alkanes and permanganate reducing compounds (PRC's). Crude product stream 121, as well as subsequent derivative streams, may contain corrosion metal contaminants that form downstream of flasher 112. Crude product stream 121 contains substantially no aromatic and/or amine compounds.

Returning to the crude acetic acid product, crude product stream 121 from flasher 112 is directed to purification section 120. In one exemplary embodiment, purification section 120 preferably comprises a light ends column 123, a drying column 140, PRC removal system (PRS) 150, and vent scrubber 160. Suitable purification sections may also comprise additional guard beds and/or heavy ends columns.

In one embodiment, light ends column 123 yields a low-boiling overhead vapor stream 126, a product side stream 127, and an optional bottoms stream 122. The temperature at the base of light ends column 123, i.e., temperature of optional exiting bottoms stream 122, preferably is from 120° C. to 170° C. In addition, the temperature at the top of the light ends column, i.e., temperature of low-boiling overhead vapor stream 126, preferably is from 100° C. to 145° C.

Low-boiling overhead vapor stream 126 may comprise methyl iodide, methyl acetate, water, PRC's, acetic acid, alkanes, and dissolved gases. As shown, low-boiling overhead vapor stream 126 preferably is condensed and directed to an overhead phase separation unit, as shown by overhead decanter 128. Conditions are desirably maintained such that the condensed low-boiling overhead vapor stream 126, once in decanter 128, will separate into a light phase and a heavy phase. The light phase and heavy phase are withdrawn via lines 129 and 130, respectively, and these streams are also referred to as process streams.

Light phase stream 129 preferably comprises water, acetic acid, and PRC's, as well as methyl iodide and methyl acetate. As shown in FIG. 1, light phase stream 129 may be refluxed to light ends column 122. A portion of light phase stream 129 may also be separated and processed in a PRS 150 to remove PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

Optionally, a portion of light phase stream 129 may also be returned to carbonylation reactor 110 via stream 131. When returned to reactor 110, light phase stream 131 may be fed to exchange resin bed 114 as slipstream 124. Heavy phase stream 130 from decanter 128 can be conveniently recirculated, either directly or indirectly, to reactor 110. A portion of heavy phase stream 130 may be fed as slipstream 124 to exchange resin bed 114 and preferably in combination with light phase stream 131. Optionally, a portion of the heavy phase 130 may be recirculated to reactor 110, with a slip stream (not shown), generally a small amount, e.g., from 5 to 40 vol. %, or from 5 to 20 vol. %, of heavy phase 130 being directed to PRS 150.

PRS 150 comprises a column 151 and extractor 152. Column 151 yields a vapor overhead stream 153 and a bottom process stream 154. Bottom process stream 154 comprises water, methyl acetate, methanol and mixtures thereof. A portion of bottom process stream 154 may be fed as slipstream 124 to exchange resin bed 114. Overhead stream 153 may be enriched in at least one PRC and may also contain methyl iodide. Overhead stream 153 is condensed and collected in an accumulator. A portion of condensed overhead stream 153 can be refluxed back to column 151 via stream 155. The remaining portion of condensed overhead stream is fed to extractor 152 via stream 156. In one embodiment, stream 156 may contain methanol and methyl acetate at a combined concentration of less than about 10 wt. %, e.g., less than about 5 wt. %, less than about 2 wt. %, or less than about 1.5 wt. %. Also stream 156 may contain less than about 3 wt. % acetic acid, e.g., less than about 1 wt. %, or less than about 0.5 wt. %.

Extraction with an aqueous stream 157, such as water, may be either a single stage or multistage extractor and any equipment used to conduct such extractions can be used in the practice of the present invention. Multistage extraction is preferred. For example, extraction can be accomplished by combining stream 156 with aqueous stream 157 and providing the combination successively to a mixer and then a separator. Multiple such combinations of mixer and separator can be operated in series to obtain a multistage extraction. Multistage extraction may be accomplished in a single vessel having a series of trays. The vessel may be equipped with paddle(s) or other mechanisms for agitation to increase extraction efficiency.

The mutual solubility between the two phases in the extraction can increase with temperature. Accordingly, it is desirable that the extraction be conducted at a combination of temperature and pressure such that the extractor contents can be maintained in the liquid state. Moreover, it is desirable to minimize the temperatures to which stream 156 is exposed to minimize the likelihood of polymerization and condensation reactions involving acetaldehyde. Water used in the extraction is desirably from an internal stream so as to maintain water balance within the reaction system. Dimethyl ether (DME) can be introduced to the extraction to improve the separation of methyl iodide in the extraction, i.e., to reduce the loss of methyl iodide into the waste stream 159. The DME can be introduced to the process or formed in situ.

In extractor 152, stream 156 is desirably provided proximate to one end of the vessel with aqueous stream 157 being provided proximate to the other end of the vessel or such other location to obtain a countercurrent flow. A waste stream 159 comprising the at least one PRC, namely acetaldehyde, is extracted by the water. Waste stream 159, in some embodiments, may strip acetaldehyde and recirculate water to the process. Raffinate, notably containing methyl iodide is withdrawn from extractor 152 as a process stream 158. A portion of raffinate 158 may be fed as slipstream 124 to exchange resin bed 114.

PRC removal columns are further described in U.S. Pat. Nos. 6,143,930, 6,339,171, and 7,223,886, and U.S. Pub. Nos. 2005/0197513, 2006/0247466, and 2006/0293537, the disclosures of which are hereby incorporated by reference. An exemplary two-stage distillation PRS comprising one or more extractors is described in U.S. Pat. No. 7,223,886. An exemplary single stage PRS, similar to those shown in FIG. 1, is described in U.S. Pub. No. 2006/0247466.

Product side stream 127 from the light ends column may comprise acetic acid and water. Product side stream 127 preferably is in the liquid phase and is withdrawn from the light ends column 123 at a temperature from 115° C. to 160° C., e.g., from 125° C. to 155° C. A portion of stream 127 may be returned to light ends column 123 via a side condenser.

Drying column 140 separates product side stream 127 to yield an overhead stream 141 comprised primarily of water and a dried product stream 142. The dried purified product stream 142 preferably comprises acetic acid in an amount greater than 90 wt. %, e.g., greater than 95 wt. % or greater than 98 wt. %. The temperature at the base of drying column 140, i.e., temperature of the exiting dried purified product stream 142, preferably is from 115° C. to 185° C., 130° C. to 180° C., e.g., from 140° C. to 175° C. The temperature at the top of drying column 140, i.e., temperature of overhead stream 141, preferably is from 90° C. to 150° C., 100° C. to 150° C., e.g., from 110° C. to 145° C. In some embodiments, the pressure in drying column 140 is from 2 bar to 7 bar, e.g., 3 bar to 6 bar, or 4 bar to 5 bar. Optionally, dried purified product stream 142 may be further treated in one or more guard beds (not shown) and/or heavy end columns (not shown) to further remove impurities, such as halides, or heavier acids and/or esters.

Overhead stream 141 of the drying column may be cooled and condensed in an overhead receiver 143 to form a light phase and a heavy phase. A portion of the light phase from receiver 143 may be refluxed to drying column 140 via line 144. The remaining portion of light phase 145 may be a process stream and fed to exchange resin bed 114 as slipstream 124. Heavy phase 146 is also a process stream that may be returned to reactor 110. A portion of heavy phase 146 may be fed as slipstream 124 to exchange resin bed 114. The condensed overhead stream 141, either as light phase 145 or heavy phase 146, is preferably used as slipstream 124 because both streams contain relatively high amounts of water.

Non-condensable gases from decanter 128 may be removed by vent stream 133 and treated in vent scrubber 160. A scrubbing solvent 161, preferably chilled to less than 25° C., may be fed to vent scrubber 160 to scrub vent stream 133 of low boiling point components, such as methyl iodide, which are removed as a process stream via line 163. A portion of low boiling point components in line 163 may be fed as slipstream 124 to exchange resin bed 114. Scrubbing solvents include methanol, methyl acetate, dimethyl ether, acetic acid and mixtures thereof. The overheads of recovery unit 160 may exit as purge gas 164 that comprises carbon monoxide and other inert gases.

Although FIG. 1 illustrates processing the catalyst-containing solution in line 113 from flasher 112 being treated to remove amines, other process streams described above may also be treated in one or more exchange resins to remove corrosive metals and/or amine compounds.

Figure 2:
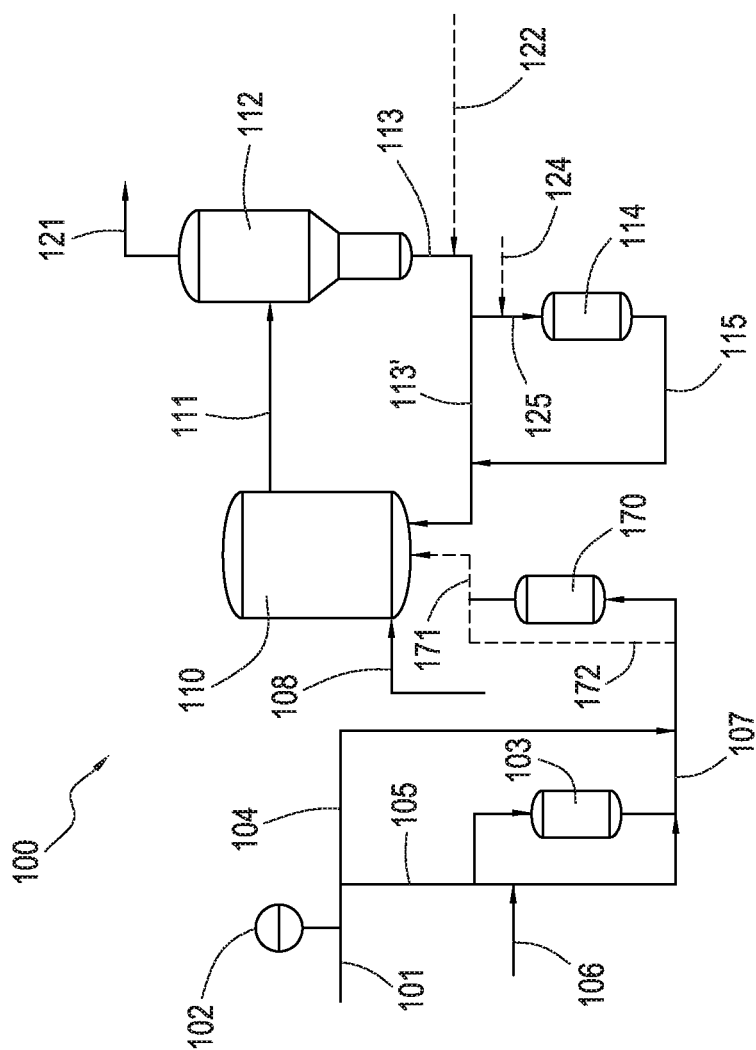
FIG. 2 illustrates a carbonylation section having a guard bed and an exchange resin for the reactant feed stream according to an embodiment of the present invention.

FIG. 1 depicts embodiments in which aromatic compounds are removed prior to the carbonylation reactor and amine compounds are removed in the presence of corrosion metal contaminants. FIG. 2 shows another embodiment in which aromatic compounds and amine compounds in the reactant feed stream 101 are removed prior to the carbonylation reactor 110. For clarity, the recovery unit 117 and purification section 120 are not illustrated in FIG. 2.

As previously indicated, reactant feed stream 101 may comprise low grades of methanol that contain amine compounds. The reactant feed stream 101 may also contain aromatic compounds. As discussed above in FIG. 1, gas chromatographer 102 measures aromatic concentration and the carbonylation process 100 determines whether to direct reactant feed stream 101 via line 104 or line 105. When aromatics are detected, the reactant feed stream in line 105 may be treated in guard bed 103 or diluted with a stream 106 to form reactant composition 107. The reactant composition is fed to exchange resin bed 170. Exchange resin bed 170 may be similar to the exchange resins described in this application. Typically there are no corrosion metal contaminants in reactant composition 107 and reactant composition 107 is generally non-acidic. A solvent, such as an aqueous slipstream, may be added to exchange resin bed 170. Exchange resin bed 170 produces an outflow 171 that is fed to reactor. The reduced amine content may be less than 1 wppm based on total weight of outflow stream 171 and more preferably outflow stream 171 is substantially free of aromatic and amine compounds. Advantageously, reaction solution 111 withdrawn from reactor 110 may be substantially free of aromatic and amine compounds. Thus, no amine compounds in the form of iodide salts build up in flasher 112. Also, exchange resin bed 114 in FIG. 2 may be used to remove corrosion metal contaminants.

Slipstream 124 in FIG. 2 is optional and may contain acetic acid to create an acidic environment to favor removal of corrosion metal contaminants when reaction solution 111 is substantially free of amine compounds. In preferred embodiments, exchange resin bed 170 may be sized to process the entire flow from reactant feed stream. However, it may be necessary to by-pass exchange resin bed 170 via line 172 to maintain reaction conditions. When reactant feed line 172 by-passes exchange resin bed 170, optional slipstream 124 may be added to create an aqueous stream 125 having a water concentration of greater than 50 wt. %.

One of ordinary skill in the art having the benefit of this disclosure can design and operate the distillation columns described herein to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

In order that the invention disclosed herein may be more efficiently understood, an example is provided below. It should be understood that these examples are for illustrative purposes only and is not to be construed as limiting the invention in any manner.

EXAMPLES

Example 1

15.9 g of a methanol feed containing 78 wppm of xylenes was pretreated in accordance with an embodiment of the present invention by passing the methanol to a guard bed containing an adsorbent. Each of the absorbents was granular activated carbon and included: Fisherbrand™ Activated Carbon Charcoal 6 to 14 mesh, Calgon SGL™ 8×30 and Calgon CAL™ 12×40. A blank was also tested. The type of adsorbent and loading of adsorbent is shown in Table 1 below. Samples were taken after the guard bed to determine the amount of xylenes left. The guard bed was maintained at a temperature from 20° C. to 35° C. The results in Table 1 demonstrate the effectiveness in reducing xylenes concentration using activated carbon adsorbents.

TABLE 1

| Adsorbent | Absorbent Wt. (g) | % of Xylenes Removed | Xylenes Remaining (wppm) |
|---|---|---|---|
| Blank | 0 | 0% | 78 |
| Fisherbrand | 0.04 | 26.9% | 57 |
| Fisherbrand | 0.1 | 50% | 39 |
| Fisherbrand | 0.21 | 71.8% | 22 |
| Fisherbrand | 0.25 | 76.9% | 18 |
| Fisherbrand | 0.5 | 93.6% | 5 |
| SGL 8 × 30 | 0.04 | 19.2% | 63 |
| SGL 8 × 30 | 0.15 | 41% | 46 |
| SGL 8 × 30 | 0.2 | 60.3% | 31 |
| SGL 8 × 30 | 0.25 | 64.1% | 28 |
| SGL 8 × 30 | 0.49 | 88.5% | 9 |
| CAL 12 × 40 | 0.04 | 23.1% | 60 |
| CAL 12 × 40 | 0.1 | 51.3% | 38 |
| CAL 12 × 40 | 0.15 | 62.8% | 29 |
| CAL 12 × 40 | 0.2 | 74.4% | 20 |
| CAL 12 × 40 | 0.26 | 79.5% | 16 |
| CAL 12 × 40 | 0.49 | 94.9% | 4 |

Example 2

A nonvolatile residue (NVR) test was used to determine the amount of non-volatiles that would deadsorb off of the adsorbent when exposed to methanol. The adsorbents were immersed in methanol and filtered off. NVR was measured by evaporating methanol. The results for the adsorbents used in Example 1 are shown in Table 2.

TABLE 2

| Adsorbent | Adsorbent Wt. (g) | MeOH Wt. (g) | MeOH in NVR Test (g) | NVR Wt. (mg) |
|---|---|---|---|---|
| CAL 12 × 40 | 15 | 45 | 20.1 | 1.5 |
| SGL 8 × 30 | 30 | 90 | 49.1 | <0.001 |
| Fisherbrand | 30 | 90 | 45.7 | 101.4 |

CAL 12×40 was further tested by repeating the methanol immersion. CAL 12×40 was immersed in 180 g of methanol and filtered off. The results for CAL 12×40 are shown in Table 3.

TABLE 3

| Adsorbent | Adsorbent Wt. (g) | MeOH Wt. (g) | MeOH in NVR Test (g) | NVR Wt. (mg) |
|---|---|---|---|---|
| CAL 12 × 40 | 60 | 180 | 79.1 | 1.3 mg |
| CAL 12 × 40 | 60 | 180 | 79.1 | <0.1 mg |
| CAL 12 × 40 | 60 | 180 | 79.1 | 0.3 mg |

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

What is claimed is:

1. A carbonylation process for producing a carbonylation product having a low aromatic content, the process comprising:
    contacting a reactant composition that comprises (i) a reactant selected from the group consisting of methanol, methyl acetate, methyl formate, dimethyl ether, and mixtures thereof and (ii) an aromatic compound, with a guard bed that comprises an adsorbent to form a de-aromatic reactant composition;
    reacting carbon monoxide with the de-aromatic reactant composition in a reactor containing a reaction medium to produce a reaction solution comprising acetic acid, and wherein the reaction medium comprises water, acetic acid, methyl acetate, methyl iodide, and a catalyst; and
    withdrawing a reaction solution from the reactor, wherein the reaction solution comprises less than 40 wppm aromatic compounds, based on the total weight of the reaction solution.

2. The process of claim 1, wherein the adsorbent is selected from the group consisting of activated carbon, zeolites, activated amorphous clays, metal oxides, and silicaceous adsorbents.

3. The process of claim 1, wherein at least 6 milligrams of the adsorbent is used for each gram of the reactant composition.

4. The process of claim 1, wherein the reactant composition comprises at least 1 wppm aromatic compounds, based on total weight of the reactant composition.

5. The process of claim 1, wherein the aromatic compound is selected from the group consisting of benzene, toluene, xylenes, ethylbenzene, naphthalene, benzene derivatives, and mixtures thereof.

6. The process of claim 1, wherein the de-aromatic reactant composition comprises less than 40 wppm the aromatic compounds, based on total weight of the de-aromatic reactant composition.

7. The process of claim 1, wherein the de-aromatic reactant composition has a lower concentration of the aromatic compounds than the reactant composition.

8. The process of claim 1, wherein at least 40% of the aromatic compounds are removed by the guard bed.

9. The process of claim 1, wherein the guard bed is adjacent to an inlet for the reactor.

10. A carbonylation process for producing a carbonylation product having a low aromatic content, the process comprising:
    measuring the concentration of aromatic compounds in a reactant composition, wherein the reactant is selected from the group consisting of methanol, methyl acetate, methyl formate, dimethyl ether, and mixtures thereof; provided that the concentration of aromatic compounds in the reactant composition is more than 1 wppm;
    contacting the reactant composition with a guard bed that comprises an adsorbent to form a de-aromatic reactant composition having less than 40 wppm, provided that the concentration of the aromatic compounds of the de-aromatic reactant composition is less than the concentration of the aromatic compounds of the reactant composition;
    reacting carbon monoxide with the de-aromatic reactant composition in a reactor containing a reaction medium to produce a reaction solution comprising acetic acid, and wherein the reaction medium comprises water, acetic acid, methyl acetate, methyl iodide, and a catalyst; and
    withdrawing a reaction solution from the reactor, wherein the reaction solution comprises less than 40 wppm aromatic compounds.

11. The process of claim 10, wherein the aromatic compounds are measured using an on-line analyzer selected from the group consisting of gas chromatography, and UV spectrophotometry.

12. The process of claim 10, further comprising adding a fresh reactant to the reactant composition prior to the guard bed, wherein the fresh reactant comprises less aromatic compounds than the reactant composition.

13. A carbonylation process for producing a carbonylation product having a low aromatic and amine content, the process comprising:
    contacting a reactant composition that comprises (i) a reactant selected from the group consisting of methanol, methyl acetate, methyl formate, dimethyl ether, and mixtures thereof, (ii) an aromatic compound, and (iii) an amine, with a guard bed that comprises an adsorbent to form a de-aromatic reactant composition;
    contacting the de-aromatic reactant composition with an exchange resin to produce a purified de-aromatic reactant composition having a reduced amine content;
    reacting carbon monoxide with the purified de-aromatic reactant composition in a reactor containing a reaction medium to produce a reaction solution comprising acetic acid, and wherein the reaction medium comprises water, acetic acid, methyl acetate, methyl iodide, and a catalyst; and
    withdrawing a reaction solution from the reactor, wherein the reaction solution comprises less than 40 wppm aromatic compounds and less than 1 wppm amine compounds based on the total weight of the reaction solution.

14. The process of claim 13, wherein the purified de-aromatic reactant composition comprises less than 1 wppm amine, based on total weight of the purified de-aromatic reactant composition.

15. The process of claim 13, wherein the reactant composition comprises less than 100 wppm of the amine, based on total weight of the reactant composition.

16. The process of claim 13, wherein the exchange resin comprises a sulfonated styrene-divinylbenzene copolymer.

17. The process of claim 13, wherein the purified de-aromatic reactant composition has a lower concentration of the aromatic compounds and amines than the reactant composition.

18. The process of claim 13, wherein the reactant composition comprises at least 1 wppm of the aromatic compound, based on total weight of the reactant composition.

19. The process of claim 13, wherein the aromatic compound is selected from the group consisting of benzene, toluene, xylenes, ethylbenzene, naphthalene, benzene derivatives, and mixtures thereof.

20. The process of claim 13, wherein the de-aromatic reactant composition comprises less than 40 wppm of the aromatic compound, based on total weight of the de-aromatic reactant composition.

* * * * *